(12) United States Patent
Ohtsuka et al.

(10) Patent No.: US 8,022,245 B2
(45) Date of Patent: Sep. 20, 2011

(54) ALPHA-FLUOROMETHOXYCARBOXYLIC ESTER, PROCESS FOR PRODUCING THE ALPHA-FLUOROMETHOXYCARBOXYLIC ESTER, AND PROCESS FOR PRODUCING SEVOFLURANE

(75) Inventors: Tatsuya Ohtsuka, Settsu (JP); Yoshichika Kuroki, Settsu (JP); Atsushi Suzuki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 455 days.

(21) Appl. No.: 12/305,467

(22) PCT Filed: Jun. 27, 2007

(86) PCT No.: PCT/JP2007/062855
§ 371 (c)(1),
(2), (4) Date: Dec. 18, 2008

(87) PCT Pub. No.: WO2008/004466
PCT Pub. Date: Jan. 10, 2008

(65) Prior Publication Data
US 2010/0010255 A1 Jan. 14, 2010

(30) Foreign Application Priority Data
Jul. 6, 2006 (JP) .................................. 2006-186208

(51) Int. Cl.
*C07C 69/66* (2006.01)
*C07C 43/00* (2006.01)

(52) U.S. Cl. ........................................ 560/184; 568/683
(58) Field of Classification Search .................. None
See application file for complete search history.

(56) References Cited

U.S. PATENT DOCUMENTS

| | | | | |
|---|---|---|---|---|
| 3,321,515 A | 5/1967 | Moore et al. | .................. | 260/544 |
| 3,544,633 A | 12/1970 | Yodis et al. | .................. | 260/593 |
| 3,683,092 A | 8/1972 | Regan et al. | .................. | 424/342 |
| 4,250,334 A | 2/1981 | Coon et al. | .................. | 568/683 |
| 5,466,879 A | 11/1995 | Cheburkov | .................. | 564/253 |
| RE35,568 E * | 7/1997 | Halpern et al. | ............... | 568/683 |
| 5,990,359 A | 11/1999 | Ryan et al. | .................. | 568/683 |
| 6,469,219 B1 | 10/2002 | Khrimian et al. | ............. | 568/683 |

FOREIGN PATENT DOCUMENTS

| | | |
|---|---|---|
| JP | 61-25694 | 6/1986 |
| JP | 61-277645 | 12/1986 |
| JP | 1-203339 | 8/1989 |
| JP | 6-184025 | 7/1994 |
| JP | 11-116521 | 4/1999 |
| JP | 2002-234860 A1 | 8/2002 |
| JP | 2002234860 * | 8/2002 |
| JP | 2002-356465 A1 | 12/2002 |
| JP | 2005-306747 | 11/2005 |
| WO | WO97/30961 | 8/1997 |
| WO | WO 03/101956 A1 | 12/2003 |

OTHER PUBLICATIONS

International Search Report for International Application No. PCT/JP2007/062855 dated Aug. 3, 2007.

* cited by examiner

*Primary Examiner* — Paul A Zucker
(74) *Attorney, Agent, or Firm* — Wenderoth, Lind & Ponack, L.L.P.

(57) ABSTRACT

The present invention provides a novel α-fluoromethoxycarboxylic ester represented by Formula (1): $(CF_3)_2C(OCH_2F)COOR$ wherein R is a hydrocarbon group that may have a substituent; a process for producing 1,1,1,3,3,3-hexafluoroisopropyl fluoromethyl ether, the process including hydrolyzing and decarboxylating the α-fluoromethoxycarboxylic ester; and a process for producing an α-fluoromethoxycarboxylic ester represented by Formula (1): $(CF_3)_2C(OCH_2F)COOR$, the process including reacting an α-hydroxycarboxylic ester represented by Formula (2): $(CF_3)_2C(OH)COOR$ with a halofluoromethane in the presence of an alkaline compound. According to the present invention, 1,1,1,3,3,3-hexafluoroisopropyl fluoromethyl ether (sevoflurane), which is known as an anesthetic compound, can be efficiently produced at low cost.

4 Claims, No Drawings

ALPHA-FLUOROMETHOXYCARBOXYLIC ESTER, PROCESS FOR PRODUCING THE ALPHA-FLUOROMETHOXYCARBOXYLIC ESTER, AND PROCESS FOR PRODUCING SEVOFLURANE

TECHNICAL FIELD

The present invention relates to a novel α-fluoromethoxycarboxylic ester that is useful as an intermediate for producing sevoflurane, a process for producing the same, and a process for producing sevoflurane using the α-fluoromethoxycarboxylic ester.

BACKGROUND ART 1,1,1,3,3,3-hexafluoroisopropyl fluoromethyl ether, represented by the chemical formula $(CF_3)_2CH(OCH_2F)$, is generally called "sevoflurane" and is known as an inhalational anesthetic. The production of sevoflurane at low cost is an important issue, and various processes therefor have been researched and developed.

For example, Patent Document 1 listed below discloses a process for producing sevoflurane wherein 1,1,1,3,3,3-hexafluoro-2-propyl methyl ether, obtained by methylation of hexafluoroisopropanol (HFIP), is reacted with chlorine gas to give 1,1,1,3,3,3-hexafluoro-2-propyl chloromethyl ether and this compound is reacted with KF in an organic solvent; a process therefor comprising reacting a 1,1,1,3,3,3-hexafluoro-2-propyl methyl ether with $BrF_3$; and a process therefor comprising reacting HFIP with hydrogen fluoride and formaldehyde.

However, the reaction in which the chloromethyl ether is fluorinated with KF has the drawback of requiring a high temperature and a prolonged reaction, and thus poses problems for implementation on an industrial scale. The process wherein the methyl ether is reacted with $BrF_3$ requires handling of the dangerous $BrF_3$, and is therefore not suitable for mass production. The process wherein HFIP is reacted with hydrogen fluoride and formaldehyde suffers from a low yield due to the formation of a polyether as a by-product.

To overcome these problems, Patent Document 3 listed below, for example, discloses a process wherein hydrogen fluoride and paraformaldehyde are reacted with HFIP in the presence of sulfuric acid. Moreover, Patent Document 2 listed below discloses a process wherein the methyl ether of HFIP is reacted with chlorine gas to produce 1,1,1,3,3,3-hexafluoro-2-propyl chloromethyl ether, which is then reacted with hydrogen fluoride and amine.

With respect to the process wherein hydrogen fluoride and paraformaldehyde are reacted with HFIP in the presence of sulfuric acid, the following inventions have further been made as processes for improving the yield.

For example, Patent Document 4 listed below discloses a process wherein a polyether compound formed as a by-product during the reaction is reacted with hydrogen fluoride and a reaction accelerator such as sulfuric acid or the like to produce Sevoflurane. Patent Document 5 listed below discloses a process wherein hydrogen fluoride and paraformaldehyde are reacted with HFIP in the presence of sulfuric acid, and the formed Sevoflurane is extracted from the equilibrium mixture by distillation or extraction, thereby increasing the yield.

Moreover, Patent Document 6 discloses a process wherein HFIP is reacted with bis(fluoromethyl)ether in the presence of acid.

In addition to the above-described processes, a number of processes for producing Sevoflurane are known, and most of these processes use HFIP as a starting material. As a process for producing HFIP, a process wherein hexafluoroacetone or its hydrate is reduced by hydrogen in the presence of a catalyst (see Patent Documents 7 and 8 listed below, etc.) is known. As processes for producing hexafluoroacetone, a process wherein hexafluoropropylene oxide is rearranged in the presence of a catalyst (Patent Document 9), and a process wherein hexachloroacetone is fluorinated with hydrogen fluoride (Patent Document 10) are known. The former process, however, has a problem in that the starting material, i.e., hexafluoropropylene oxide, is expensive. The latter process also has problems in that the purification processes for separating the resulting hexafluoroacetone from hydrochloric acid, for separating the byproduct chlorofluoroacetone, and the like are complicated, making the process costly.

In view of these circumstances, attempts have been made to produce hexafluoroacetone at low cost. Processes that are attracting attention, in particular, are those using, as starting materials, $(CF3)_2CHCF_2OCH_3$ (2H-octafluoroisobutyl methyl ether; hereinafter abbreviated to "OIME") obtained by reacting methanol with octafluoroisobutene which is a by-product of hexafluoropropene that is mass-produced as a monomer for fluororesins, $(CF_3)_2C=CFOCH_3$ (heptafluoroisobutenyl methyl ether; hereinafter abbreviated to "HIME") obtained by removing HF from OIME, and the like.

Patent Document 11, for example, discloses a process for producing hexafluoroacetone hydrate, wherein HIME is reacted with oxygen under light irradiation.

Patent Document 12 discloses a process for producing hexafluoroacetone or its hydrate, wherein OIME or HIME is reacted with oxygen in the presence of an activated carbon catalyst.

Patent Document 13 discloses a process for producing hexafluoroacetone, wherein OIME is reacted with triethylamine to give hexafluoroacetone oxime, which is then hydrolyzed with acid.

Patent Document 14 discloses a process for producing hexafluoroacetone hydrate, wherein $(CF_3)_2C(OH)CO_2CH_3$ (methyl 3,3,3-trifluoro-2-trifluoromethyl-2-hydroxypropionate; hereinafter abbreviated to "MTTHP") is hydrolyzed and then decarboxylated by reacting the hydrolysis product with a halogenating agent.

The process utilizing the photo-oxidation of HINE, however, has problems in that it is difficult to industrially perform light irradiation, and that the yield is low. The oxidation process using an activated carbon catalyst has problems such as inability to perform a long-term operation due to significant degradation of the catalyst, a low selectivity of hexafluoroacetone, and the like. The process wherein OIME is reacted with triethylamine to give an oxime has a problem in that triethylamine, which is an auxiliary starting material, is expensive. The process wherein MTTHP is hydrolyzed and then decarboxylated by halogenation uses an inexpensive auxiliary starting material and has a high yield, but it has the drawback of requiring a large number of steps.

Processes for producing HFIP at low cost without using the intermediate hexafluoroacetone have been contemplated as follows.

For example, Patent Document 15 discloses a process for producing HFIP, comprising synthesizing MTTHP by oxidation of HIME, hydrolyzing the resulting MTTHP, and decarboxylating the hydrolysis product in the presence of a protonic solvent. As a result of re-examination performed by the inventors, however, this process was found to have a low yield because of the formation of $CF_3(HCF_2)C=O$ (pentafluoroacetone) as a by-product during decarboxylation.

As described above, although the production of hexafluoroacetone or HFIP at low cost is an important issue, satisfactory results have yet to be obtained. Accordingly, in order to produce Sevoflurane at low cost, there is a strong desire for the development of a process for producing hexafluoroacetone or HFIP at low cost, or the development of a process for producing Sevoflurane without using these intermediates.

Patent Document 1: U.S. Pat. No. 3,683,092
Patent Document 2: Japanese Unexamined Patent Publication No. 11-116521
Patent Document 3: U.S. Pat. No. 4,250,334
Patent Document 4: WO 97/30961
Patent Document 5: U.S. Pat. No. 6,469,219
Patent Document 6: U.S. Pat. No. 5,990,359
Patent Document 7: Japanese Examined Patent Publication No. 61-25694
Patent Document 8: Japanese Unexamined Patent Publication No. 6-184025
Patent Document 9: U.S. Pat. No. 3,321,515
Patent Document 10: U.S. Pat. No. 3,544,633
Patent Document 11: Japanese Unexamined Patent Publication No. 61-277645
Patent Document 12: Japanese Unexamined Patent Publication No. 1-203339
Patent Document 13: U.S. Pat. No. 5,466,879
Patent Document 14: Japanese Unexamined Patent Publication No. 2005-306747
Patent Document 15: Japanese Unexamined Patent Publication 2002-234860

DISCLOSURE OF THE INVENTION

Problem To Be Solved By the Invention

The present invention has been made in view of the problems of the prior art. A primary object of the invention is to provide: a process of efficiently and inexpensively producing 1,1,1,3,3,3-hexafluoroisopropyl fluoromethyl ether (sevoflurane), known as an anesthetic compound; a novel compound useful to produce 1,1,1,3,3,3-hexafluoroisopropyl fluoromethyl ether; and a process for producing the novel compound.

Means For Solving the Problem

To achieve the above object, the present inventors carried out extensive research. As a result, the inventors found that when a known compound, 3,3,3-trifluoro-2-trifluoromethyl-2-hydroxypropionic ester is used as a starting material, and the hydroxyl group thereof is reacted with a fluoromethylating agent, a novel α-fluoromethoxycarboxylic ester can be obtained. The inventors further found that when the α-fluoromethoxycarboxylic ester is hydrolyzed under alkaline or acidic conditions, decarboxylation proceeds simultaneously with hydrolysis, and the desired 1,1,1,3,3,3-hexafluoroisopropyl fluoromethyl ether (sevoflurane) can be produced at a high yield by a comparatively simple method. The present invention has been accomplished based on this finding.

More specifically, the present invention provides an α-fluoromethoxycarboxylic ester, a process for producing the α-fluoromethoxycarboxylic ester, and a process for producing 1,1,1,3,3,3-hexafluoroisopropyl fluoromethyl ether (sevoflurane) from the α-fluoromethoxycarboxylic ester, as summarized below.

1. An α-fluoromethoxycarboxylic ester represented by Formula (1):

$$(CF_3)_2C(OCH_2F)COOR \quad (1)$$

wherein R is a hydrocarbon group that may have at least one atom selected from the group consisting of halogen, oxygen, nitrogen, and sulfur atoms.

2. A process for producing 1,1,1,3,3,3-hexafluoroisopropyl fluoromethyl ether represented by the chemical formula $(CF_3)_2CH(OCH_2F)$, the process comprising hydrolyzing and decarboxylating an α-fluoromethoxycarboxylic ester represented by Formula (1):

$$(CF_3)_2C(OCH_2F)COOR \quad (1)$$

wherein R is a hydrocarbon group which may have at least one atom selected from the group consisting of halogen, oxygen, nitrogen, and sulfur atoms.

3. The process for producing 1,1,1,3,3,3-hexafluoroisopropyl fluoromethyl ether according to Item 2, wherein the α-fluoromethoxycarboxylic ester represented by Formula (1) is hydrolyzed and decarboxylated under alkaline or acidic conditions.

4. A process for producing an α-fluoromethoxycarboxylic ester represented by Formula (1):

$$(CF_3)_2C(OCH_2F)COOR \quad (1)$$

wherein R is a hydrocarbon group which may have at least one atom selected from the group consisting of halogen, oxygen, nitrogen, and sulfur atoms, the process comprising reacting an α-hydroxycarboxylic ester represented by Formula (2):

$$(CF_3)_2C(OH)COOR$$

wherein R is as defined above with a halofluoromethane represented by Formula (3):

$$CH_2FX$$

wherein X is Cl or Br under alkaline conditions.

A novel α-fluoromethoxycarboxylic ester that is useful as an intermediate for producing 1,1,1,3,3,3-hexafluoroisopropyl fluoromethyl ether, and a process for producing the α-fluoromethoxycarboxylic ester are described below first. Subsequently, a process for producing 1,1,1,3,3,3-hexafluoroisopropyl fluoromethyl ether from the α-fluoromethoxycarboxylic ester is described.

Novel Fluoromethyl Ether Ester Compound and Production Process Thereof

A novel α-fluoromethoxycarboxylic ester that is useful as an intermediate for producing 1,1,1,3,3,3-hexafluoroisopropyl fluoromethyl ether can be produced by using as a starting material an a-hydroxycarboxylic ester represented by Formula (2): $(CF_3)_2C(OH)COOR$ wherein R is a hydrocarbon group that may have at least one atom selected from the group consisting of halogen, oxygen, nitrogen, and sulfur atoms. The compound represented by Formula (2) is a known compound, and is described, for example, in Japanese Unexamined Patent Publication No. 2002-234860.

Examples of the hydrocarbon group represented by R in Formula (2) include hydrocarbon groups, such as a $C_1$-$C_{10}$ alkyl group, an aryl group, and an aralkyl group. Examples of preferable alkyl groups include a methyl group, an ethyl group, an isopropyl group, a t-butyl group, a hexyl group, and the like. Examples of preferable aryl groups include a phenyl group, a naphthyl group, a pyridyl group, a chlorophenyl group, and the like. Examples of preferable aralkyl groups include a benzyl group, a phenethyl group, and the like. Among these, a methyl group is particularly preferable from the viewpoint of low-cost production.

According to the present invention, a novel α-fluoromethoxycarboxylic ester represented by Formula (1):

$(CF_3)_2C(OCH_2F)COOR$ wherein R is as defined above can be obtained by reacting an α-hydroxycarboxylic ester represented by Formula (2) with a halofluoromethane represented by Formula (3): $CH_2FX$ (wherein X is Cl or Br) under alkaline conditions. As described below, the obtained α-fluoromethoxycarboxylic ester is subjected to hydrolysis and decarboxylation reactions to obtain the desired 1,1,1,3,3,3-hexafluoroisopropyl fluoromethyl ether (sevoflurane) at a high yield.

Methods of reacting a phenolic hydroxyl group or thiol with chlorofluoromethane to produce a fluoromethyl ether, a fluoromethyl thioether, or the like are known (see, for example, Chem. Ber., 118(6) (1985), 2208-2219; J. Org. Chem., 44 (1979), 1708-1711). However, a method of fluoromethylating an alcoholic hydroxyl group is not known. To develop a method of synthesizing sevoflurane, the present inventors studied fluoromethylation of hexafluoroisopropanol (HFIP) by reacting HFIP with an inexpensive chlorofluoromethane; however, the production of sevoflurane was not observed. Nonetheless, the inventors unexpectedly found that when an α-hydroxycarboxylic ester represented by Formula (2): $(CF_3)_2C(OH)COOR$ is used as a starting material, the α-hydroxycarboxylic ester can easily react with a halofluoromethane, such as chlorofluoromethane under alkaline conditions to thereby produce a fluoroinethyl ether.

Examples of the alkaline compound used in the reaction of an α-hydroxycarboxylic ester represented by Formula (2) with a halofluoromethane represented by Formula (3): $CH_2FX$ include hydroxides, hydrides, oxides, carbonates, hydrogen carbonates, and alcoholates of alkali metals (e.g., Li, K, Na) or alkaline earth metals (e.g., Mg, Ca, Ba). Such alkaline compounds can be used singly or in a combination of two or more types.

The amount of alkaline compound used is about 0.5 to about 5 equivalents, preferably about 1 to about 3 equivalents, and even more preferably about 1 to about 2 equivalents, per equivalent of the α-hydroxycarboxylic ester represented by Formula (3).

In the above reaction, a polar solvent is preferably used as a reaction solvent. Examples of preferable polar solvents include dimethylformamide, dimethyl sulfoxide, N-methylpyrrolidone, acetonitrile, tetrahydrofuran, glyme, diglyme, triglyme, tetraglyme, methyl ethyl ketone, acetone, methanol, ethanol, isopropyl alcohol, ethylene glycol, diethylene glycol, triethylene glycol, water, and the like. Mixtures of the above compounds can also be used as the solvent. Dimethylformamide is particularly preferable.

Although the reaction temperature may vary depending on the kind of halofluoromethane used, it is usually in the range of about 0° C. to about 100° C. However, when the reaction temperature is high, methyl ether represented by Formula (4): $(CF_3)_2C(OCH_3)CO_2R$ is easily formed as an undesirable by-product. When the reaction temperature is low, the generation of methyl ether as a by-product can be inhibited, but it takes a longer time to complete the reaction due to a reduced reaction rate. Considering the above, the reaction temperature is preferably in the range of about 10° C. to about 60° C.

The reaction time is usually in the range of about 10 hours to about 40 hours. If the reaction is performed at a low temperature for an excessively short time, the hydroxycarboxylic ester of Formula (2) used as a starting material remains unreacted, resulting in a low yield. Therefore, it is necessary to set an appropriate reaction time according to the reaction temperature.

The ester represented by Formula (1) is a novel compound not yet described in the literature. This compound is useful as an intermediate for producing 1,1,1,3,3,3-hexafluoroisopropyl fluoromethyl ether.

Method of Producing Hexafluoroisopropyl Fluoromethyl Ether (Sevoflurane)

According to the present invention, an α-fluoromethoxycarboxylic ester represented by Formula (1): $(CF_3)_2C(OCH_2F)COOR$ wherein R is as defined above is hydrolyzed and decarboxylated to produce 1,1,1,3,3,3-hexafluoroisopropyl fluoromethyl ether (sevoflurane) represented by the chemical formula $(CF_3)_2CH(OCH_2F)$.

This reaction can be performed by subjecting an α-fluoromethoxycarboxylic ester represented by Formula (1) to hydrolysis and decarboxylation under alkaline or acidic conditions. In this reaction, it is considered that an α-fluoromethoxycarboxylic ester represented by Formula (1) is hydrolyzed to produce a carboxylic acid represented by the chemical formula: $(CF_3)_2C(OCH_2F)COOH$, or a salt thereof, which is then decarboxylated to produce 1,1,1,3,3,3-hexafluoroisopropyl fluoromethyl ether (sevoflurane). The carboxylic acid represented by the chemical formula $(CF_3)_2C(OCH_2F)COOH$ or a salt thereof is promptly decarboxylated under the hydrolysis conditions to produce the desired 1,1,1,3,3,3-hexafluoroisopropyl fluoromethyl ether (sevoflurane).

The hydrolysis and decarboxylation reactions can be performed, for example, by a method comprising adding an aqueous alkaline or acidic solution to an α-fluoromethoxycarboxylic ester represented by Formula (1); or a method comprising adding α-fluoromethoxycarboxylic ester represented by Formula (1) to an aqueous alkaline or acidic solution.

The alkaline compound to be used is not particularly limited, and examples thereof include hydroxides, hydrides, oxides, carbonates, hydrogen carbonates, and alcoholates of alkali metals (e.g., Li, K, Na), or alkaline earth metals (e.g., Mg, Ca, Ba). Such alkaline compounds can be used singly or in a combination of two or more types. The acid to be used is not particularly limited, and examples thereof include inorganic acids such as sulfuric acid, nitric acid, hydrochloric acid, hydrobromic acid, and phosphoric acid; and organic acids such as acetic acid and formic acid. Such acids can be used singly or in a combination of two or more types.

The amount of alkaline compound used is not particularly limited, and may be about 0.05 to about 5 equivalents, preferably about 0.2 to about 2 equivalents, and even more preferably about 0.5 to about 1 equivalent, per equivalent of the α-fluoromethoxycarboxylic ester represented by Formula (1).

The amount of acid used is not particularly limited, and may be about 0.05 to about 10 equivalents, preferably about 0.2 to about 2 equivalents, and even more preferably about 0.5 to about 1 equivalent, per equivalent of the α-fluoromethoxycarboxylic ester represented by Formula (1).

The reaction temperature is usually in the range of about 0° C. to about 100° C., and preferably about 20° C. to about 50° C. An excessively low reaction temperature results in a low reaction rate. Therefore, such a temperature is not preferable.

The reaction time may be usually in the range of about 1 to about 10 hours.

The ester compound represented by Formula (1) may be isolated before it is subjected to hydrolysis and decarboxylation reactions, or a mixture of the ester compound with a by-product methyl ether of Formula (4): $(CF_3)_2C(OCH_3)CO_2R$ generated in the production of the ester compound may be used as is. When the mixture is used as a starting material, 1,1,1,3,3,3-hexafluoroisopropyl fluoromethyl ether (sevoflurane) can be produced directly after the production of an α-fluoromethoxycarboxylic ester represented by Formula (1) from an α-hydroxycarboxylic ester represented by Formula (2): $(CF_3)_2C(OH)COOR$. Therefore, the production process can be shortened. In this case, the hydrolysis rate of the α-fluoromethoxycarboxylic ester of Formula (1) is greatly different from and much higher than that of the compound of Formula (4). Therefore, if the reaction is performed at a low temperature, the compound of Formula (4) can be recovered in an unreacted state. However, if the reaction temperature is too high, the compound of Formula (4) is also hydrolyzed and decarboxylated, so that the desired 1,1,1,3,3,3-hexafluoroisopropyl fluoromethyl ether as well as by-products such as 1,1,1,3,3,3-hexafluoroisopropyl methyl ether and 1,1,1,3,3-pentafluoro-2-methoxypropene derived from the compound of Formula (4) are produced, which makes it difficult to purify the 1,1,1,3,3,3-hexafluoroisopropyl fluoromethyl ether. Therefore, care regarding the reaction temperature is necessary.

When an α-fluoromethoxycarboxylic ester represented by Formula (1) is subjected to hydrolysis and decarboxylation reactions, 1,1,1,3,3,3-hexafluoroisopropyl fluoromethyl ether can be obtained with very high selectivity almost quantitatively.

An alcohol represented by ROH is generated as a hydrolysate in the above reaction. The alcohol represented by ROH can be easily removed from the desired 1,1,1,3,3,3-hexafluoroisopropyl fluoromethyl ether by washing with water.

1,1,1,3,3,3-hexafluoroisopropyl fluoromethyl ether obtained by the above method can be separated and purified by known methods; the ether can be purified, for example, by distillation, extraction, or like methods.

EFFECT OF THE INVENTION

According to the present invention, an α-fluoromethoxycarboxylic ester represented by Formula (1), which is a novel compound and useful as an intermediate for producing anesthetic sevoflurane (1,1,1,3,3,3-hexafluoroisopropyl fluoromethyl ether), can be obtained at a high yield by using a known hydroxycarboxylic ester represented by Formula (2) as a starting material.

The α-fluoromethoxycarboxylic ester can be efficiently converted into sevoflurane by hydrolysis and decarboxylation reactions.

Therefore, according to the present invention, sevoflurane can be efficiently produced at low cost by using a known α-hydroxycarboxylic ester as a starting material.

BEST MODE FOR CARRYING OUT THE INVENTION

The following Examples serve to illustrate the invention in more detail.

EXAMPLE 1

Preparation of Fluoromethyl Ether Compound

A solution of 169.5 g (0.75 mol) of $(CF_3)_2C(OH)CO_2CH_3$ (methyl 3,3,3-trifluoro-2-trifluoromethyl-2-hydroxypropionate) (MTTHP) in DMF (451 g) and 103.7 g (0.75 mol) of potassium carbonate were charged into a 1 liter-capacity autoclave. After the reactor was sealed and then deaerated, 52 g (0.75 mol) of fluorochloromethane was introduced at an internal temperature of 20° C. to 30° C.

After 30 minutes, the temperature was increased to 50° C., and 61 g (0.89 mol) of fluorochloromethane was added while carefully watching for the generation of heat. The mixture was stirred at a temperature of 60° C. for 3 hours, and then cooled to room temperature.

The obtained reaction solution was analyzed by F-NMR. The conversion of the starting material was 87%. The selectivity of the desired $(CF_3)_2C(OCH_2F)CO_2CH_3$ was 43%. $(CF_3)_2C(OCH_3)CO_2CH_3$ was obtained as a by-product with a selectivity of 22%.

Spectral data of $(CF_3)_2C(OCH_2F)CO_2CH_3$:

MS spectrum: 239 (M$^+$-19), 211, 199, 189, 180, 159, 147, 131, 128, 97, 81, 69, 63, 59, 45, 33, 29, 15

$^{19}$F-NMR spectrum: 72.41 ppm (s, 6F), 151.43 (t, 1F)

$^{1}$H-NMR: δ 5.72 ppm (d 2H), 4.05 ppm (s 3H).

EXAMPLE 2

A reaction was performed in the same manner as in Example 1, except that the reaction temperature used was in the range of 20° C. to 30° C., and the reaction time was 125 hours.

The obtained reaction solution was analyzed in the same manner as in Example 1. The conversion was 90%. The selectivity of the desired $(CF_3)_2C(OCH_2F)CO_2CH_3$ was 44%. The selectivity of the methylated compound $((CO_3)_2C(OCH_3)CO_2CH_3)$ obtained as a by-product was 20%.

EXAMPLE 3

Reactions were performed in the same manner as in Example 1, except that the reaction temperatures used were 30° C., 50° C., and 80° C., and the reaction time was 4 hours. The obtained reaction mixtures were analyzed by F-NMR using an internal standard. Table 1 below shows the results (yields).

TABLE 1

| Reaction temperature | $(CF_3)_2C(OCH_2F)CO_2CH_3$ | $(CF_3)_2C(OCH_3)CO_2CH_3$ |
|---|---|---|
| 30° C. | 8.2% | 0.4% |
| 50° C. | 26.5% | 4.1% |
| 80° C. | 22.4% | 18.4% |

EXAMPLE 4

Hydrolysis and Decarboxylation Reactions

A mixture of $(CF_3)_2C(OCH_2F)CO_2CH_3$ (10.03 mmol, 2.59 g), $(CF_3)_2C(OCH_3)CO_2CH_3$ (6.98 mmol, 1.68 g) and $(CF_3)_2C(OH)CO_2CH_3$ (3.27 mmol, 0.74 g) was added to a two-necked flask equipped with a Dimroth condenser, and stirred with heating at 50° C. A 30% aqueous KOH solution (23.04 mmol, 4.31 g) was slowly added dropwise, and the mixture was stirred at the same temperature for 2 hours.

After cooling, the organic layer (lower layer) and water layer (upper layer) separated from each other were analyzed by F-NMR using an internal standard. Table 2 below shows the results.

TABLE 2

| | Organic layer (lower layer) | Water layer (upper layer) |
|---|---|---|
| 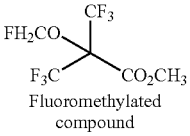<br>Fluoromethylated compound (FH$_2$CO–C(CF$_3$)(F$_3$C)–CO$_2$CH$_3$) | 0.18 mmol (2% recovery) | 0 |
| 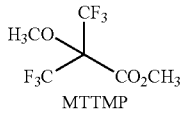<br>MTTMP (H$_3$CO–C(CF$_3$)(F$_3$C)–CO$_2$CH$_3$) | 1.48 mmol (21% recovery) | 0 |
| 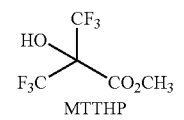<br>MTTHP (HO–C(CF$_3$)(F$_3$C)–CO$_2$CH$_3$) | 0 | 0 |
| 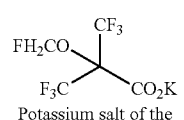<br>Potassium salt of the fluoromethylated compound (FH$_2$CO–C(CF$_3$)(F$_3$C)–CO$_2$K) | 0 | 0 |
| 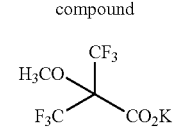<br>Potassium salt of MTTMP (H$_3$CO–C(CF$_3$)(F$_3$C)–CO$_2$K) | 0 | 4.94 mmol (71% yield) |
| 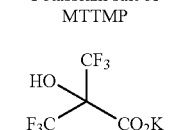<br>Potassium salt of MTTHP (HO–C(CF$_3$)(F$_3$C)–CO$_2$K) | 0 | 3.25 mmol (99% yield) |
| 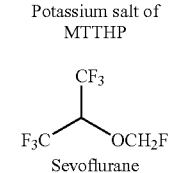<br>Sevoflurane ((CF$_3$)$_2$CH–OCH$_2$F) | 8.85 mmol (89% yield) | 0 |
| 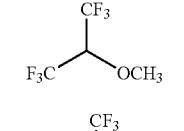<br>(CF$_3$)$_2$CH–OCH$_3$ | 0.33 mmol (5% yield) | 0 |
| 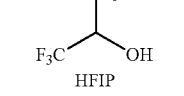<br>HFIP ((CF$_3$)$_2$CH–OH) | 0 | 0 |

The above results clearly show that even when a fluoromethylated compound represented by Formula (1) is used in the form of a mixture of a methylated compound and a hydroxide, sevoflurane can be obtained at a high yield by hydrolysis and decarboxylation reactions.

Comparative Example 1

A solution of 2.0 g (11.9 mmol) of (CF$_3$)$_2$CH(OH) (hexafluoroisopropanol)(HFIP) in DMF (1.3 ml) and 1.63 g (12.2 mmol) of potassium carbonate were charged into a 10 ml-capacity autoclave. After the reactor was sealed and then deaerated, 1.7 g (24.8 mmol) of fluorochloromethane was introduced.

The mixture was heated to 60° C. and stirred for 3 hours, and then cooled to room temperature.

The obtained reaction solution was analyzed by F-NMR, and the analysis showed no production of 1,1,1,3,3,3-hexafluoroisopropyl fluoromethyl ether (sevoflurane).

Reactions were performed in the same manner as above, except that the reaction temperatures used were 80° C. and 100° C. No sevoflurane was obtained.

The invention claimed is:

1. An α-fluoromethoxycarboxylic ester represented by Formula (1):

(CF$_3$)$_2$C(OCH$_2$F)COOR   (1)

wherein R is a hydrocarbon group that may have at least one atom selected from the group consisting of halogen, oxygen, nitrogen, and sulfur atoms.

2. A process for producing 1,1,1,3,3,3-hexafluoroisopropyl fluoromethyl ether represented by the formula (CF$_3$)$_2$CH(OCH$_2$F), the process comprising hydrolyzing and decarboxylating an α-fluoromethoxycarboxylic ester represented by Formula (1):

(CF$_3$)$_2$C(OCH$_2$F)COOR   (1)

wherein R is a hydrocarbon group that may have at least one atom selected from the group consisting of halogen, oxygen, nitrogen, and sulfur atoms.

3. The process for producing 1,1,1,3,3,3-hexafluoroisopropyl fluoromethyl ether according to claim 2, wherein the α-fluoromethoxycarboxylic ester represented by Formula (1) is hydrolyzed and decarboxylated under alkaline or acidic conditions.

4. A process for producing an α-fluoromethoxycarboxylic ester represented by Formula (1):

(CF$_3$)$_2$C(OCH$_2$F)COOR   (1)

wherein R is a hydrocarbon group that may have at least one atom selected from the group consisting of halogen, oxygen, nitrogen, and sulfur atoms, the process comprising reacting an α-hydroxycarboxylic ester represented by Formula (2):

(CF$_3$)$_2$C(OH)COOR wherein R is as defined above with a halofluoromethane represented by Formula (3):

CH$_2$FX   (3)

wherein X is Cl or Br under alkaline conditions.

* * * * *